(12) United States Patent
Stacey et al.

(10) Patent No.: US 6,369,179 B1
(45) Date of Patent: Apr. 9, 2002

(54) 2-FLUOROACRYLATE ESTER POLYMERS AND USE THEREOF AS OPTICAL MATERIALS

(75) Inventors: Nicholas A. Stacey, High Easter; Alastair S. Dodds; Luke C. Williams, both of Hartolo, all of (GB)

(73) Assignee: Minnesota Mining and Manufacturing Company, Saint Paul, MN (US)

( * ) Notice: Subject to any disclaimer, the term of this patent is extended or adjusted under 35 U.S.C. 154(b) by 0 days.

(21) Appl. No.: 09/434,771

(22) Filed: Nov. 4, 1999

Related U.S. Application Data

(63) Continuation of application No. 08/346,083, filed on Nov. 29, 1994, now Pat. No. 6,018,008.

(30) Foreign Application Priority Data

Jan. 4, 1994 (GB) .............................................. 9400016

(51) Int. Cl.[7] .................................................. C08F 18/20
(52) U.S. Cl. ....................... 526/245; 385/143; 385/142; 358/901.1
(58) Field of Search .......................... 526/245; 385/142, 385/143; 358/901.1

(56) References Cited

U.S. PATENT DOCUMENTS

| | | | |
|---|---|---|---|
| 4,720,166 A | 1/1988 | Ohmori et al. | 350/96.34 |
| 4,971,424 A | 11/1990 | Babirad et al. | 350/96.34 |
| 5,111,526 A | 5/1992 | Yamamoto et al. | 385/145 |
| 5,148,511 A | 9/1992 | Savu et al. | 385/145 |

FOREIGN PATENT DOCUMENTS

| | | | |
|---|---|---|---|
| AU | A-13035/88 | 3/1987 | |
| EP | 0 128 516 | 6/1984 | C08F/220/22 |
| FR | 2 623 510 | 11/1987 | C08F/20/22 |
| WO | WO 93/03074 | 2/1993 | C08F/20/24 |

OTHER PUBLICATIONS

G2: Inks; Paint; Polishes. p. 15.
Appl. Phys. Lett. 42 (7), Apr. 1, 1983. "Low Loss Poly-(methlmethacrylate–d8) core optical fibers", Kaino et al., p. 567–569.
Journal of Fluorine Chemistry, 55 (1991) 149–162. "Synthese con ∞–Fluoracrylsäure und Derivaten".
Macromolecules 1980, 13, 1031–1036. "Synthesis and Polymerization of Methyl ∞–Fluorozcrylate", Pittman et al.

Primary Examiner—Robert Dawson
Assistant Examiner—Kuo-Liang Peng
(74) Attorney, Agent, or Firm—John A. Fortkort; Nestor F. Ho; Alan Ball

(57) ABSTRACT

1H,1H-perfluorocyclohexylmethyl 2-fluoroacrylate, and homopolymers thereof.

2 Claims, 1 Drawing Sheet

2-FLUOROACRYLATE ESTER POLYMERS AND USE THEREOF AS OPTICAL MATERIALS

Figure 1:
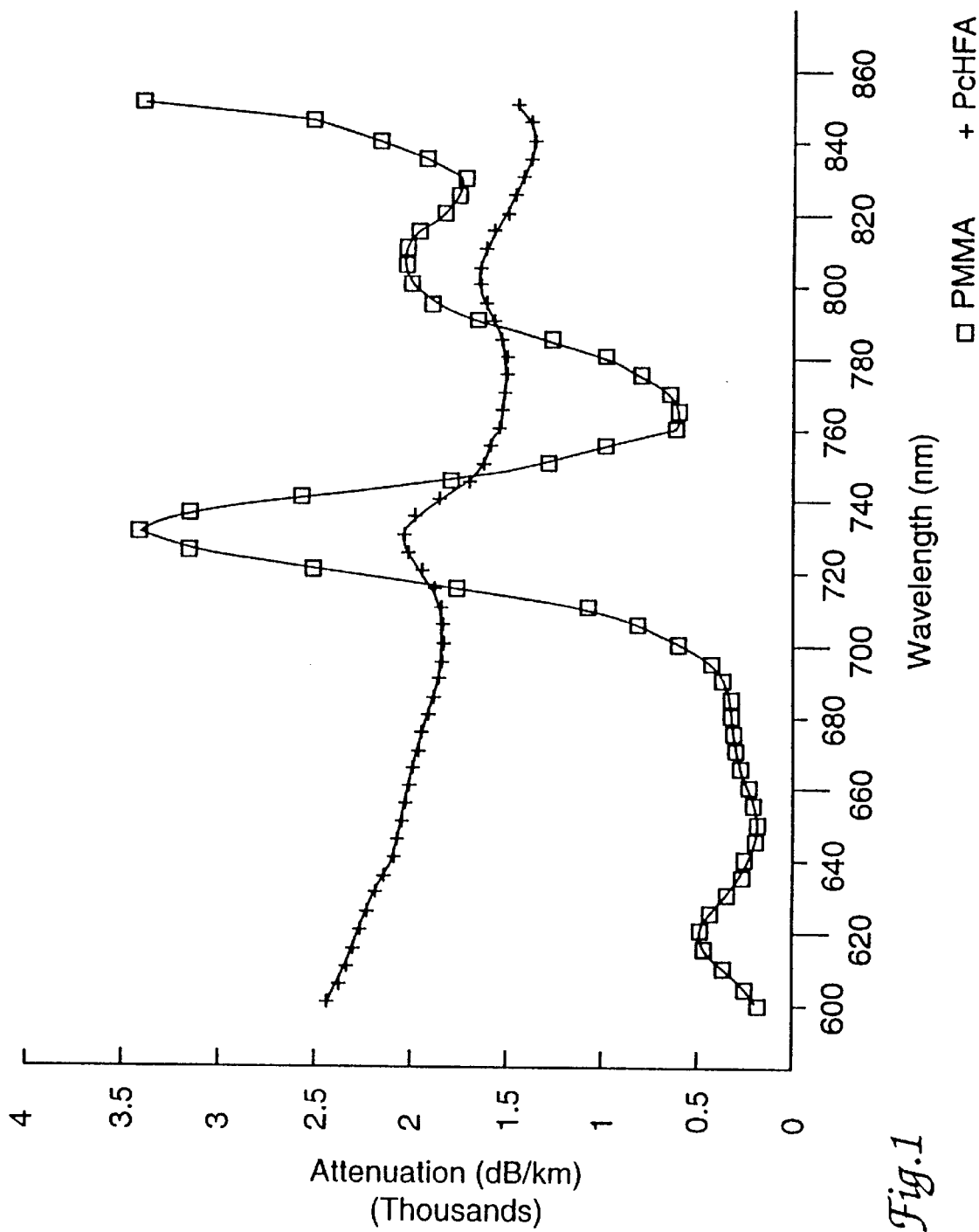

This is a continuation of application Ser. No. 08/346083 filed Nov. 29, 1994, now U.S. Pat. No. 6,018,008.

FIELD OF THE INVENTION

This invention relates to the ester of 2-fluoroacrylic acid with 1H,1H,-perfluorocyclohexyl-methanol and to homopolymers and copolymers thereof and to the use of such polymers in optical materials, particularly optical fibres.

BACKGROUND OF THE INVENTION

Plastic optical fibres have attracted much interest and been an area of active commercial research for many years since they offer the potential of combining the rapid data transmission advantages afforded by glass optical fibres with the ruggedness and low costs associated with copper cabling products.

Despite this activity and interest, plastic optical fibres, (POFs) have not, to date, been widely accepted as a data communications medium. One of the key contributing factors in delaying this acceptance has been the poor thermal stability of available fibres. Data transmission systems in both automotive and aerospace applications provide large markets for POFS. However, underbonnet applications in automobiles require extended performance above 100° C., with many aerospace environments even more severe and demanding performance at temperatures in excess of 140° C. The upper use temperature for current commercial POFS, which are predominantly based on polymethyl methacrylate [PMMA] and polystyrene [PS], is about 80° C., which is too low for these applications. The high temperature performance of a polymer for these applications is limited by its glass transition temperature (Tg), since at temperatures around and above Tg its mechanical and optical properties decline. For both PMMA and PS, Tg is in the range of 100° C. to 105° C. Thus, materials with Tgs above those of PMMA and PS are desirable to increase the maximum use temperature of the resulting POFS.

A further factor delaying the acceptance of POFs has been the high optical attenuations of currently available commercial fibres to transmission in the red and near infrared (NIR) region, where preferred solid state light sources operate. The fabrication of plastic optical fibres with lower attenuations in these regions is an area of current polymer fibre research.

The predominant contributor to the red and NIR optical attenuation of most amorphous polymeric materials suitable for optical fibres is absorption caused by overtone and combination bands of the C—H bond's fundamental vibration. The academic and patent art has therefore concentrated on reducing these attenuations and this has been achieved by partial or complete replacement of H atoms by the heavier deuterium or halogen atoms. This reduces NIR attenuations due to the higher reduced mass of the C—X bond (X=D,F, Cl) compared to the C—H bond, so shifting the fundamental and overtone frequencies out of the range of interest.

The replacement of H with D has received much attention and has produced very good results (Appl.Phys.Let. 1983, 42, 567). Attenuations as low as 20 dB/Km (650 nm) have been obtained from fully deuterated PMMA fibres. Unfortunately, cost considerations of deuteration make this approach essentially of academic interest only, and there has been no attempt to commercialise a fibre containing deuterium.

Halogenation represents a much more commercially attractive option to reducing attenuations. By introduction of these heavier atoms, the effect of hydrogen overtones can be reduced and/or diluted and so attenuations may be reduced in a similar manner to deuteration. Whilst both chlorine and bromine substituted polymers have been considered, the advantages associated with fluorination, namely, C—F bond stability, low atomic bulk etc., have made this approach the most attractive.

For a number of reasons, mainly related to fabrication and processing, optical polymers are predominantly acrylic ester based materials. Fluorination in such systems has been largely achieved by the use of short-chain perfluorinated ester methacrylates, taking advantage of the readily available short chain perfluoroalcohols. A review of this art is disclosed in WO 93/03074. The attenuation improvements available from such materials, particularly in the NIR can be significant. The above document discloses materials with NIR attenuations approximately 25% of those of conventional PMMA fibres. However, in order to reduce attenuations substantially further, not only must the side chain ester functionality of the polymer be fluorinated, but it is also necessary to replace the hydrogen atoms of the polymer backbone. One of the most effective methods of achieving this is to replace the methyl function of the methacrylate backbone with a fluorine atom, producing 2-fluoroacrylate polymers. As well as reducing the polymer H-atom content, this approach also has the advantage that, by careful choice of the side-chain group, the Tg of the polymer may be increased to a level where it may be suitable for high temperature usage. The combination of high Tg, leading to a high upper use temperature, and a high degree of fluorination, giving the potential for very low optical losses, yields materials which show much promise as optical fibre core materials for local area networks where the use conditions are severe, for example in automobile and aerospace applications.

Esters of 2-fluoroacrylic acid are well known. The methyl ester of 2-fluoroacrylic acid can be prepared by the reaction of methyl 2-fluoroacetate with formaldehyde in the presence of calcium hydride and dimethyl oxalate,as disclosed in Macromolecules 1980, 13, 1031–1036. The polymerisation of this monomer, methyl 2-fluoroacrylate (MFA), is reported to give a high Tg (128° C.) polymer.

Several methods are known for the preparation of other derivatives of 2-fluoroacrylic acid e.g. J. Fluorine Chem. 1991, 55, 149–162. For example, 2Hoctafluorocyclopentyl methyl 2-fluoroacrylate may be prepared from 2,3-difluoropropionyl chloride by a two-step reaction in which the acid chloride is dehydrofluorinated to give the 2-fluoroacryloyl chloride, then treated with 1H,lH,2H-octafluoropentyl methanol in the presence of base. There is no disclosure of polymerisation of this or other monomers although reference is made to the good general optical and physical properties of 2-fluoroacrylic ester polymers.

It is known that polymers containing 2-fluoroacrylate esters may be used for the preparation of optical fibre cores. EP-0128516 discloses monomers of the formula $H_2C=CF—COOR_f$, in which Rf is a fluorinecontaining aliphatic group, preferably a fluorinecontaining lower alkyl group. Examples are given of 2-fluoroacrylate homopolymers with glass transition temperatures up to 125° C. [poly (3H-1,1-dimethyltetrafluoropropyl 2-fluoroacrylate)]. JP 02092908 discloses 2-fluoroacrylates in which the backbone C—H bonds are replaced by C—D bonds to reduce the NIR bond absorptions. The monomers have the formula $D_2C=CR^1—COOR^2$ in which $R^1$ is F, D, or $CD_3$, and $R^2$ is $CnY2n+1$ (Y=F, Cl) Lower alkyl chains only are exemplified.

Monomers and polymers of 2-fluoroacrylates with fluorinated rings are disclosed in FR 2623510. However, the examples and claims relate only to fluorinated aromatic materials.

AU-A-13035/88 discloses 2-fluoroacrylate materials in which a substituted bicyclic ring is present. The monomer structure allows the possibility of bicyclic perfluorinated 2-fluoroacrylate esters, however, all examples relate to chlorinated monomers. The patent recommends specifically chlorine, bromine or trifluoromethyl substitution, but discloses no perfluorinated rings.

Other examples of polymers of alicyclic highly fluorinated (meth)acrylic monomers are known as optical materials. W093/03074 discloses a specific monomer, H1H,1H-perfluorocyclohexylmethyl methacrylate, and homopolymers and copolymers thereof with other fluorinated and non-fluorinated monomers, as an optical fibre core with low optical loss. However, high temperature usage is not disclosed.

U.S. Pat. No. 5,148,511 discloses cladding compositions comprising copolymers of fluorine containing methacrylate monomers with methyl methacrylate. Glass transition temperatures of up to 108° C. are indicated for solution copolymers of 1H,1H-perfluorocyclohexylmethyl methacrylate with methyl methacrylate in 50:50 weight ratio.

The present invention provides alternative fluorinecontaining materials suitable for the preparation of optical elements.

SUMMARY OF THE INVENTION

According to one aspect of the invention there is provided 1H,lH-perfluorocyclohexylmethyl 2-fluoroacrylate. According to a further aspect of the invention there is provided a homopolymer or copolymer of 1H,1H-perfluorocyclohexylmethyl 2-fluoroacrylate.

DESCRIPTION OF PREFERRED EMBODIMENTS

Depending on the intended use and desired physical properties, the copolymer may comprise, in addition to 1H,1H-perfluorocyclohexylmethyl 2-fluoroacrylate, any addition-polymerisable monomer, such as acrylic acid, methacrylic acid, 2-fluoroacrylic acid and esters, amides and nitrites derived therefrom, including mixtures of these monomers. For optical fibre applications, the copolymer is preferably formed from:

a) at least 40%, preferably at least 60% by weight of 1H,1H-perfluorocyclohexylmethyl 2-fluoroacrylate and b) up to 60% by weight, preferably 0 to 40% by weight of a copolymerisable monomer selected from the group consisting of methyl 2-fluoroacrylate, 1H,1H-perfluorooctyl 2-fluoroacrylate, 1H,1H-perfluoro(2s(butoxy)propyl) 2-fluoroacrylate, or other similar monomers, or a mixture of such monomers.

The polymers of this invention may be used to form the core of plastic optical fibres e.g. by the techniques disclosed in W093/03074. Generally the process for the preparation of POFs comprises the following steps:

a) the monomer mixture, together with a free radical initiator and chain transfer agent, is placed in a closed reaction vessel;

b) the polymerisable mixture is degassed;

c) the temperature of the vessel is raised, resulting in polymerisation of the monomer mixture;

d) the polymer is extruded into a fibre core generally having a diameter in the range of 0.1 to 2.0 mm.

The plastic fibres of the invention exhibit NIR attenuations which are significantly lower than the best commercially available materials based on PMMA (typical losses about 3000 dB/km at 840 nm). To a first order of approximation, attenuations in such fibres can be related to the H atom concentration in relation to PMMA. By carrying out such a calculation, it is estimated that the attenuation of fibres of this invention should be approximately 150 dB/km at 840 nm. Further, whilst PMMA attenuations are highly sensitive to small wavelength drifts of the light source in this region, the fluorinated fibre of this invention is comparatively insensitive to these effects.

However the key advantage of using the perfluorocyclohexyl functionality stems from the observation that this grouping can also impart high glass transitions (about 140° C.) to the resulting polymers and fibres. This is an important feature; straight or branched perfluoroalkyl side chains are not able to achieve the high glass transitions afforded by this polymer. These Tgs are comparable to many fibres claimed for use in high temperature applications. Polycarbonates (Tg 130 to 160° C.), for example, have been used as high temperature POFS, but these materials can not be bulk polymerised from a pure monomer mixture and contain contaminants which are difficult to eliminate from the polymer, resulting in high optical attenuations in the fibres produced. Alkyl methacrylates with alicyclic substituents (e.g. bornyl, fenchyl, menthyl) have also been used for high temperature fibres; again their properties are not acceptable for low attenuation applications due to their high C—H bond content and is resulting high optical losses.

In comparison with these other polymers which have been used as high temperature POFS, the materials of this invention show a very desirable combination of properties. Additionally, high degradation temperatures (about 350° C.) are generally observed in 2-fluoroacrylate polymers, which aids their processing and increases thermal stability above that observed for their methacrylate analogues.

In addition, the fibres of the invention have excellent physical properties when compared to other highly fluorinated polymer materials which have been reported as low attenuation materials. Those described in WO93/03074, for example, where the perfluorocyclohexyl functionality is substituted onto a methacrylate backbone, are lower in modulus and more brittle than those of this invention.

The physical properties, together with a high degree of thermal stability (both in terms of upper use temperature and decomposition temperature), and potential for low attenuation, give a combination of properties which have not been reported previously for any comparable material.

The polymers of the invention could also find utility in the preparation of other high performance optical components e.g. optical fibre claddings, lenses and other forms of waveguides, where similar properties are desirable. 1H,1H-perfluorocyclohexylmethyl 2-fluoroacrylate may be prepared according to modifications of standard literature procedures (Synthesis, 1985, 754; J.Org.Chem. 1989, 54, 5640), as outlined in either Scheme 1 or Scheme 2.

Scheme 1

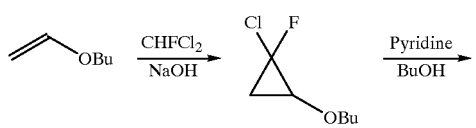

-continued

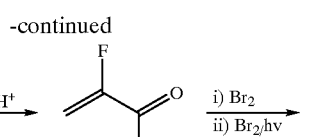

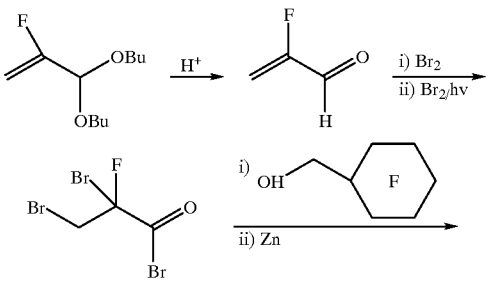

Scheme 2

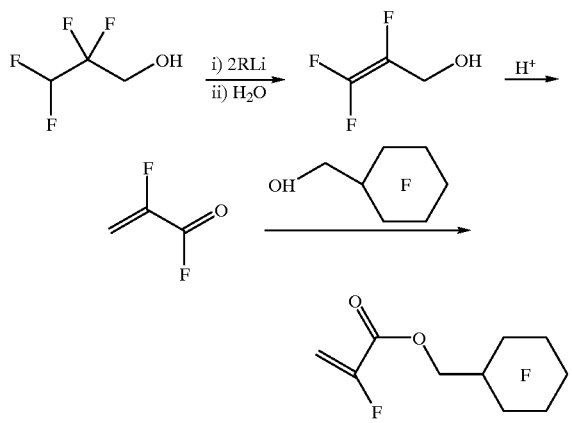

in which

represents perfluorocyclohexyl

The invention will now be illustrated by the following Examples:

EXAMPLE 1 a) Preparation of [1H,1H-perfluorocyclohexylmethyl 2,3-dibromo-2-fluoropropanoate] 2,3-dibromo-2-fluoropropanoyl bromide (158 g, 0.5mol) was added dropwise to a stirred solution of 1H,1Hperfluorocyclohexylmethanol (150 g, 0.48 mol) and triethylamine (53.3 g, 0.52 mol) in dichloromethane (250 ml) at 0° C. The mixture was allowed to attain room temperature and was then stirred overnight. Work-up was achieved by washing with water (3 ×250 ml) and brine (250 ml). After drying (MgSO,) and removing solvents under a vacuum, the organic residue was chromatographed through basic alumina 10 using a 40–60° C. petroleum spirit fraction as the eluent. Removal of solvents left the title compound as a crude oil (yield =233 g).

b) Preparation of 1H,1H-perfluorocyclohexylmethyl 2-fluoroacrylate by Scheme 1

Zinc powder (36 g, 0.5 mol) was added to diisopropyl ether (175 ml) and the mixture was purged with argon. The reaction mixture was brought to reflux and 1H,1H-perfluorocyclohexymethyl 2,3-dibromo-2fluoropropanoate (100 g, 0.18 mol) was added dropwise. Reflux was continued for six hours before the reaction mixture was allowed to cool. Zinc was removed by filtration and solvents were removed under vacuum. The residue was redissolved in ether (250 ml) and washed with water (2×100 ml), brine (100 ml) and then dried (MgSO₄). After removal of solvents, a small quantity of phenothiazine inhibitor (10 mg) was added and the crude mixture was distilled, to give the title compound (yield–72 g, Bpt. 45–65° C./0.5 mmHg) as a clear oil. Further purification of the material for use in optical fibre applications was carried out by fractional distillation, giving a pure sample of the desired monomer (Bpt.70–73° C./12 mBar).

c) Preparation of 1H,1H-perfluorocyclohexylmethyl 2 fluoroacrylate by Scheme 2

2-Fluoroprop-2-enoyl fluoride (16.2 g, 1.1 eq) was dissolved in dichloromethane (100 ml) and the solution was cooled to −50° C., with stirring. To this was added, dropwise, a solution of 1H,1H-perfluorocyyclohexylmethanol (50 g, 1 eq)triethylamine (17.45g, 1.1 eq) and N,N-dimethylaminopyridine (10 mol%) in dichloromethane (100 ml). On complete addition (20 minutes approximately), the yellow reaction mixture was allowed to attain room temperature over 2 hours, before stirring overnight. Work-up of the reaction mixture at this stage was carried out by dilution of the mixture (200 ml dichloromethane) and washing of the organic phase with water (2×100 ml), dilute hydrochloric acid (2×50 ml, 1 M), water (2×100 ml) and brine (100 ml). The organic phase was dried (Na₂SO₄) and evaporated under vacuum to give a crude oil, purified by distillation to give the title compound (yield 55 g, Bpt. 62–74 ° C./12 mBar). Again, further purification in a similar manner to that described above, was used to purify the monomer to the level required for optical fibre preparation.

EXAMPLE 2

Preparation of Poly (1H,1H-perfluorocyclohexylmethyl 2-fluoroacrylate) and processing to optical fibre. The monomer was bulk polymerized in glass preform tubes as described in WO93/03074, using t-butylhydroperoxide as initiator (0.1 mol%) and butanethiol as chain transfer agent (0.2 mol%). The monomer was degassed in the preform tube using the method of freeze/thawing until a minimum of bubbles were generated in the monomer on thawing. The polymerisation was carried out in a fluidised sand bath under the following conditions:

Initial temperature 138° C., 16 hours; ramp to 160° C. at 10° C./minutes and hold for 24 hours. On completion of the polymerisation, the preform was transferred to a fibre drawing tower such that minimum cooling occurred. The initial temperature of the drawing furnace was 180° C. and an overpressure of 0.16 atmosphere of nitrogen was applied to the top of the preform. The furnace temperature was increased in 2–3° C. increments until the polymer showed onset of flow (207° C.). Fiber was drawn at a haul-off rate of 1.0 m/min. Attenuation measurements were made on the fibre by the method of cut backs (similar to that of BS6558 Part 1—Optical Fibers and Cables); laser light was injected into the end of the fibre and several cutbacks were made.

The optical attenuation, measured using a Bentham Spectrophotometer and corrected to the laser measured attenutation recorded at 633 nm, showed a typical value of approximately 1400 dB/Km in the important 840 nm window.

The accompanying FIG. 1 indicates the attenuation spectrum for poly (1H,1H-perfluorocyclohexylmethyl 2-fluoroacrylate), compared with that for PMMA. This shows that a large scatter wedge is present for the former material compared to the optimised PMMA fibre. Even so, the optical losses for the material of this invention are significantly lower than those of PMMA at wavelengths above 800 nm.

The fibre was analysed for physical properties such as tensile strength, elongation etc; these details are given below:

| Modulus | Tensile Strength (at yield) | Elongation (at yield) |
|---|---|---|
| 1500 MPa | 44.0 MPa | 4.7% |

Thermal analysis was also carried out on samples of the material produced above. The glass transition temperature, measured by differential scanning calorimetry at a ramp rate of 10° C./min, was 138° (midpoint); the decomposition onset was measured as 360° C. by thermogravimetry, using a ramp rate of 30° C. /min in a $N_2$ atmosphere.

Example 3 (comparative)

Poly(methyl methacrylate)

The monomer was bulk polymerised in a similar manner to that used in Example 2, using 2,21-azobis(t-butane) as initiator (0.1 mol%.) and butanethiol as chain transfer agent (0.25 mol%). After degassing the mixture, polymerisation was carried out in a silicone oil bath under the following conditions initial temperature 130° C., 16 hours; ramp to 160° C. at 10° C./hour, hold for 4 hours; ramp to 180° C. at 10° C./hour, hold for 4 hours. The preform was transferred to a drawing furnace at 180° C., and an-overpressure of $N_2$ was applied (0.3 atm). The temperature was increased to 202° C., and fibre was drawn from the tip of the vessel at 3 m/min. The optical attenuation was measured by similar techniques to those used in Example 2 giving an attenuation of about 2500 db/km at 840. nm.

| Modulus | Tensile Strength (at yield) | Elongation (at yield) |
|---|---|---|
| 3070 MPa | 112 MPa | 3.6% |

Thermal analysis was also carried out, giving a glass transition temperature of 105° C. and a decomposition onset of 290° C.

Example 4 (comparative)

Poly (1H,1H-perfluorocyclohexylmethyl methacrylate)

The monomer was bulk polymerised, and then processed to an optical fibre in a similar manner to that used in W093/03074, Example 5.

Attenuation measurements made on the fibre indicated that the optical attenutation at 840 nm was approximately 850 db/km.

Analysis of the physical properties of the polymer fibre was not attempted due to the extreme brittleness of the fibre produced. However, thermal analysis was carried out, giving a glass transition temperature of 80° C. and a decomposition onset of 200° C.

Example 5 (comparative)

Poly (1H,1H-perfluorocyclohexylmethyl methacrylate-co-methyl methacrylate)

The monomers (ratio by weight 70:30, 1H,1H-perfluorocyclohexylmethyl methacrylate:methylmethacrylate) were bulk polymerised, and then processed to an optical fibre in a similar manner to that used in W093 03073, Example 1.

Attenuation measurements made on the fibre indicated that the optical attenuation at 840 nm was approximately 1000 db/km.

Analysis of the physical properties of the polymer fibre attempted by similar methods to those used in Example 1. The results are given below:

| Modulus | Tensile Strength (at yield) | Elongation (at yield) |
|---|---|---|
| 680 MPa | 17.2 MPa | 4.5% |

Thermal analysis was carried out, giving a glass transition temperature of 93° C. and a decomposition onset of 250° C.

The data given in the Examples illustrates the advantages of POFs made from poly (1H,1H-perfluorocyclohexylmethyl 2-fluoroacrylate) in accordance with the invention.

Compared to PMMA, the fibres of the invention show a higher Tg and decomposition onset, with reduced attenuation in the NIR region, and the potential for far lower attenuations with optimisation of the polymerisation and process conditions.

It can be seen that fibres of the present invention display improved thermal and physical properties in comparison with fibres described in Examples 4 and 5, which are based on methacrylate functionalised polymers.

What is claimed is:

1. 1H,1H-perfluorocyclohexylmethyl 2-fluoroacrylate.

2. A homopolymer of 1H,1H-perfluorocyclohexylmethyl 2-fluoroacrylate.

* * * * *

UNITED STATES PATENT AND TRADEMARK OFFICE
CERTIFICATE OF CORRECTION

PATENT NO.   : 6,369,179 B1
DATED        : April 9, 2002
INVENTOR(S)  : Stacey, Nicholas A.

It is certified that error appears in the above-identified patent and that said Letters Patent is hereby corrected as shown below:

Title page,
Item [57], ABSTRACT,
Line 2, after "thereof:" insert -- The copolymers may comprise monomers selected from:
    a) at least 40% by weight of 1H, 1H-perfluorocyclohexylmethyl 2-fluoroacrylate, and
    b) up to 60% by weight of monomer which is a member selected from the group consisting of methyl 2-fluoroacrylate, 1H,1H-perfluorooctyl 2-fluorocrylate, 1H,1H-perfluoro(2-(butoxy)propyl) 2-fluoroacrylate and combinations thereof.
The polymers are useful for making optical elements, particularly optical fibres. --

Column 3,
Line 14, "H1H" should read -- 1H --.

Column 6,
Line 6, "perfluorocyclohexymethyl" should read -- perfluorocyclohexylmethyl --.
Line 25, "perfluorocyyclohexylmethane" should read
-- perfluorocyclohexylmethane --.

Column 7,
Line 47, after "840 nm" add -- Analysis of the physical properties of the polymer fibres was also carried out by similar methods to those used in Example 2. The results are given below: --

UNITED STATES PATENT AND TRADEMARK OFFICE
CERTIFICATE OF CORRECTION

PATENT NO. : 6,369,179 B1
DATED : April 9, 2002
INVENTOR(S) : Stacey, Nicholas A.

It is certified that error appears in the above-identified patent and that said Letters Patent is hereby corrected as shown below:

<u>Column 8,</u>
Line 23, "WO 93 03073" should read -- WO 93/03074 --.

Signed and Sealed this

Twelfth Day of November, 2002

*Attest:*

*Attesting Officer*

JAMES E. ROGAN
*Director of the United States Patent and Trademark Office*